United States Patent [19]

Terry et al.

[11] Patent Number: 5,058,579
[45] Date of Patent: Oct. 22, 1991

[54] TRACHEOSTOMY DRESSING

[76] Inventors: Deborah A. Terry; John T. Terry, both of 11975 W. 155th St., Orland Park, Ill. 60462

[21] Appl. No.: 564,793

[22] Filed: Aug. 9, 1990

[51] Int. Cl.$^5$ .................. A61F 13/00; A61L 15/00; A61M 16/00
[52] U.S. Cl. ........................ 128/207.14; 128/155; 128/156
[58] Field of Search ............ 128/155, 156, 200.26, 128/207.14, 207.16, 207.17

[56] References Cited

U.S. PATENT DOCUMENTS

| | | | |
|---|---|---|---|
| 2,054,768 | 3/1934 | Gale Jr. | 128/155 |
| 3,286,713 | 2/1965 | Kurtz et al. | 128/156 |
| 3,422,817 | 4/1966 | Mishkin et al. | 128/207.14 X |
| 3,677,250 | 7/1972 | Thomas . | |
| 4,085,752 | 4/1978 | Canale | 128/155 X |
| 4,221,215 | 9/1980 | Mandelbaum | 128/155 |
| 4,231,370 | 11/1980 | Mroz et al. | 604/361 |
| 4,362,841 | 12/1982 | Minatono | 128/156 X |
| 4,753,231 | 6/1988 | Lang et al. | 128/155 X |

OTHER PUBLICATIONS

The Lippincott Manual of Nursing Practice (4th Ed.) Chapter 7, pp. 218-221.
Maroon (1982) Current Therapeutic Research 31(3):251-255.
Gerson et al. (1983) Laryngoscope 93:1225.
Eaglstein et al. (1984) Clinics in Dermatology 2(3):112-115.

Primary Examiner—David J. Isabella
Assistant Examiner—Elizabeth M. Burke
Attorney, Agent, or Firm—Keil & Weinkauf

[57] ABSTRACT

A tracheostomy dressing comprising an occlusive adhesive-backed dressing, a means for securing a tracheostomy tube to the occlusive dressing and a means for attaching a absorbent pad for collecting tracheal secretions to the occlusive dressing. The tracheostomy dressing is both tie-less and gauze-less and provides advantages of a functional as well as a cosmetic nature.

10 Claims, 4 Drawing Sheets

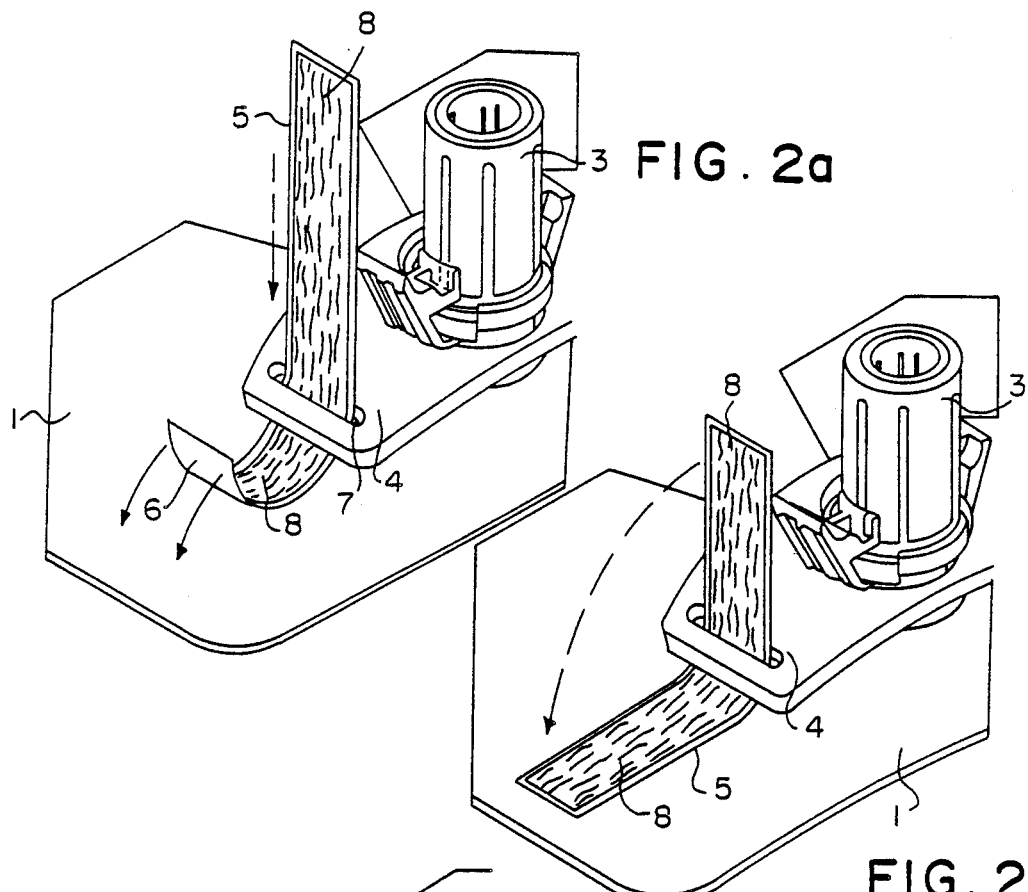
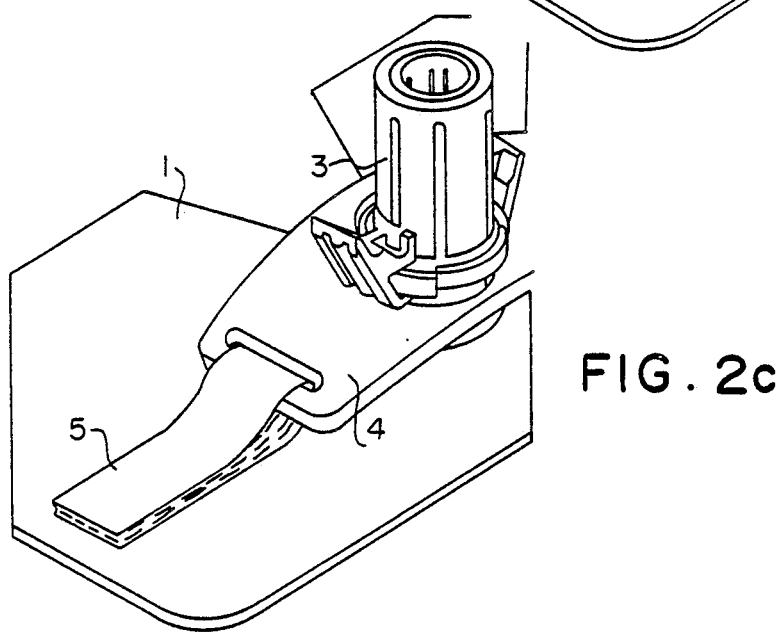
FIG. 2a
FIG. 2b
FIG. 2c

TRACHEOSTOMY DRESSING

FIELD OF INVENTION

This invention relates to a tracheostomy dressing. More particularly, the invention relates to a tracheostomy dressing that is tie-less, gauze-less and which encourages the flow of tracheal secretions away from the tracheal site. The tie-less, gauze-less dressing discourages infection and skin irritation and promotes healing.

BACKGROUND OF INVENTION

A tracheotomy is an operation wherein a physician makes an incision into the neck and trachea of a patient. A tracheostomy tube, through which the patient will breath, is then inserted by the physician into the trachea through the incision. Tracheostomy tubes are required in cases where breathing through the nose or mouth has become impossible. While man tracheostomies are of a temporary nature, others are permanent.

To keep the tracheostomy tube from dislodging and/or falling out, for example, when the patient forcefully coughs, the tube is typically secured by cloth straps or ties attached to or through slotted flanges extending from the periphery of the tracheostomy tube. The straps or ties are then fastened together at the back of the neck of the wearer. A 4" by 4" square gauze bandage cut into an "upside-down pants" configuration is placed at the neck region about the tracheostomy tube which protrudes from the tracheal stoma. At this location, the gauze dressing is used to collect mucous and tracheal secretions.

While patients receive tracheostomies for a number of reasons, the benefits are not without risks. The number one risk being the risk of infection. Even a minor infection can increase a patient's hospital stay 5 to 7 days. Serious infection can lead to other complications and even death.

The use of cloth straps or ties to secure the tracheostomy tube to the patient, to prevent expulsion of the tube, and a gauze dressing at the tracheal site, to absorb tracheal secretions and debris around the stomal site, poses a number of problems.

The ties are disadvantageous in that they not only become soiled, but also become wet with tracheal secretions as well as with perspiration. The ties are uncomfortable to many patients and, especially when wet, can cause skin irritation and breakdown around the patient's neck. When wetness is coupled with irritation, the opportunity for infection is present. In addition, the ties are not aesthetically pleasing. This cosmetic drawback is particularly important when the tracheostomy is of a permanent nature and the patient is forced to return home and enter the community with the tracheostomy tub intact.

The gauze that is placed around the tracheal stoma to absorb secretions during the healing process is problematic in that skin irritation and/or infection can result from the secretion-soaked gauze. Not only does the secretion-soaked gauze act to irritate the skin and hinder healing of the stomal area, but the moist, warm environment is an excellent medium for bacteria to grow and infect the patient through the stomal opening. Such an infection may lead to serious complications, including pneumonia. If the patient does become infected, there is a risk that the infection could spread to other patients as well as to hospital personnel. In order to help reduce or prevent irritation and infections, the gauze must be frequently changed and the tracheal stoma site cleansed. Moreover, the gauze, like the ties, has a poor cosmetic appearance.

Traditional tracheostomy dressings employing the aforementioned ties and gauze dressing are additionally disadvantageous in terms of cost effectiveness. In order to prevent the incidence of infection and irritation, the stomal area needs to be cleansed and the ties and gauze dressing changed every 8 hours, and as often as every 2 hours during the twenty-four hours immediately following surgery. Not only are frequent changes required, but such changes require the services of two health care professionals. One nurse must hold the tracheostomy tube in place while another nurse attends to cleansing and replacing the soiled ties and gauze dressing.

Alternative methods to dress a patient who has had a tracheotomy have been sought. Experiments have been conducted which use an occlusive adhesive-backed dressing. An occlusive dressing is one that is impermeable to the passage of air and moisture. The back of the occlusive dressing contains a skin sensitive adhesive which adheres to the throat around the tracheal stoma. It has been found that the use of such a dressing promotes healing of the tracheal area. While occlusive dressings have been used to surround the tracheal opening and have been shown to promote healing, they have all been used in conjunction with conventional ties. Further, the occlusive dressings of the prior art completely surround the tracheal opening and include no means of collecting tracheal secretions. As such, the occlusive dressing must be peeled off daily and replaced. No method has been developed for securing the tracheostomy tube and collecting the tracheal secretions which sufficiently overcomes the prior art method.

BRIEF DESCRIPTION OF THE INVENTION

The present invention is directed to a self-adhesive, tie-less, gauze-less tracheostomy dressing. The tracheostomy dressing comprises an occlusive, adhesive-backed dressing which contains a pre-cut circular tracheostomy opening through which the tracheal tube may pass and from which a pre-cut inverted V-shaped drainage slot extends. The pre-cut drainage slot acts to channel secretions away from the tracheal site. A tracheostomy tube, containing conventional slotted flanges is secured to the occlusive dressing by means of reclosable adhesive-backed anchoring tapes. A secretion-absorbing pad containing selfadhesive straps is removably secured to the occlusive dressing to collect secretions. The tracheostomy dressing of the present invention promotes healing of the tracheal stomal area, prevents incidents of infection, avoids the frequent changing of soiled ties and gauze, reduces the cost of patient care and is more comfortable and cosmetically superior to the prior art tracheostomy dressings.

BRIEF DESCRIPTION OF THE DRAWINGS

FIG. 2 illustrates how the tracheostomy tube is secured to the occlusive dressing.

DETAILED DESCRIPTION OF THE INVENTION

The object of the present invention is to provide a tracheostomy dressing which promotes tracheal stomal healing. It is also an object of the present invention to increase the efficiency of the dress changing procedure and to provide a tracheostomy dressing which is more comfortable and cosmetically acceptable to the wearer.

The tracheostomy dressing of the invention makes use of an occlusive membrane to promote healing. The use of an occlusive membrane as a tracheostomy dressing promotes healing and dispenses with the gauze-type tracheostomy dressing of the prior art. The occlusive dressing is adapted so as to enable the tracheostomy tube to be secured to the wearer without the need for ties and is further adapted to encourage the flow of tracheal secretions away from and distal to the tracheal stomal site. The tracheal secretions are then collected in an absorptive pad which is attached to the occlusive dressing.

More particularly, the invention is based on the use of a specially designed adhesive-backed occlusive pectin based dressing. Since an occlusive dressing is impermeable to the passage of air and moisture, it acts as a barrier to tracheal secretions. This feature enhances stomal healing by preventing secretions, which may contain infectious agents, from coming in contact with the tracheal stomal site. Non-absorbent occlusive materials, such as those commonly known in the art as Stomaadhesive or Comfeel Brand, may be used.

Figure 1:
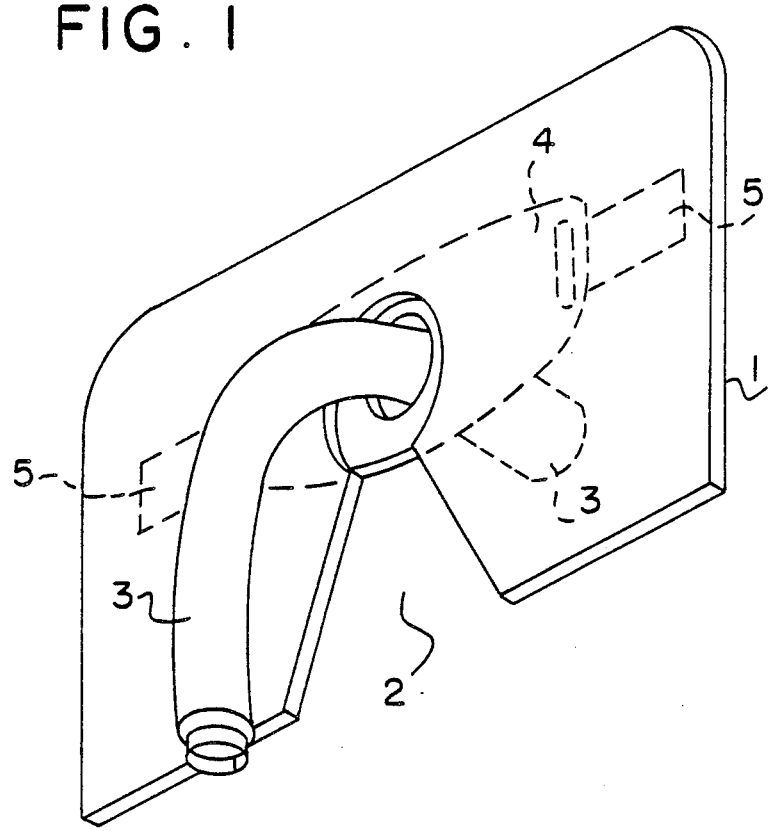
FIG. 1 is a posterior view showing the adhesive surface side of the occlusive dressing.

As can be seen in drawing FIG. 1, the adhesive-backed occlusive dressing (1) of the invention is specifically designed so as to contain a pre-cut, "key-hole" shaped area (2) comprising a circular opening from which an inverted V-shape drainage slot extends caudally. Following insertion of a conventional tracheostomy tube (3), which is manufactured so as to contain slotted flanges (4), the circular opening of the occlusive dressing is placed around the stomal site between the neck and slotted flanges of the tracheostomy tube and pressed onto the neck so that the skin-sensitive adhesive back-side of the occlusive dressing adheres to the skin. The adhesive backing allows the dressing to be applied directly to the skin around the patient's tracheal site. The tracheostomy tube is tie-lessly secured into place by the use of two adhesive-backed reclosable strips (5) using the existing slots on the tracheostomy flange of a conventional tracheostomy tube.

FIG. 2 further illustrates the tie-less feature of the invention. Half of the bottom or first side of each strip contains an adhesive with a peel-away strip. The peel-away strip is removed at the time of installation to expose an adhesive surface (6) which is used to attach the strip to the occlusive dressing. The other half, which remains unattached, is passed through the slot (7) in the slotted tracheostomy flange (4). The top or second side of each strip has a reclosable self-fastening means (8) which, when folded back on itself, secures the tracheostomy tube to the occlusive dressing. Hook and loop fasteners, such as VELCRO, are conveniently and preferably used for this purpose. FIGS. 2(a), 2(b) and 2(c) illustrate sequentially how the tracheostomy tube may be secured to the occlusive dressing in a tie-less fashion by passing the unattached side of the strip through the slot of the tracheostomy flange and fastening it to the secured side.

Figure 3:
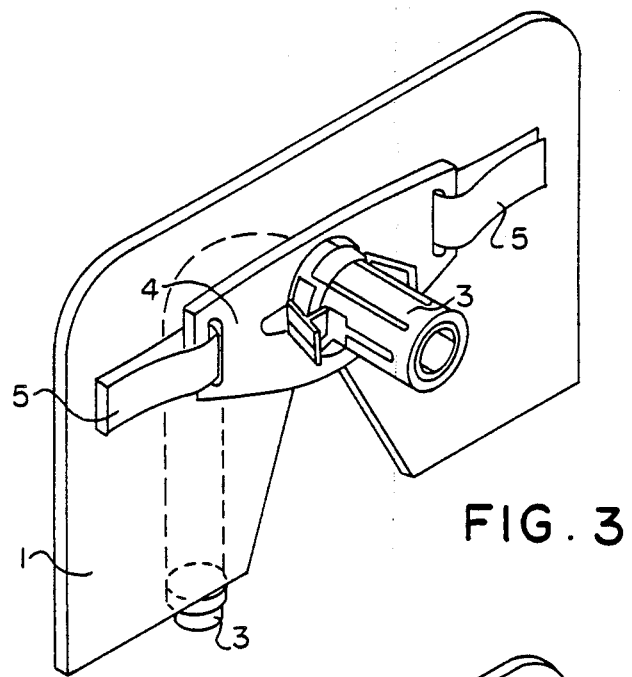
FIG. 3 is a frontal view comprising tracheostomy tube secured to an occlusive dressing.

FIG. 3 shows a tracheostomy dressing with the tracheostomy tube (3) tie-lessly secured to the occlusive dressing (1).

Figure 4:
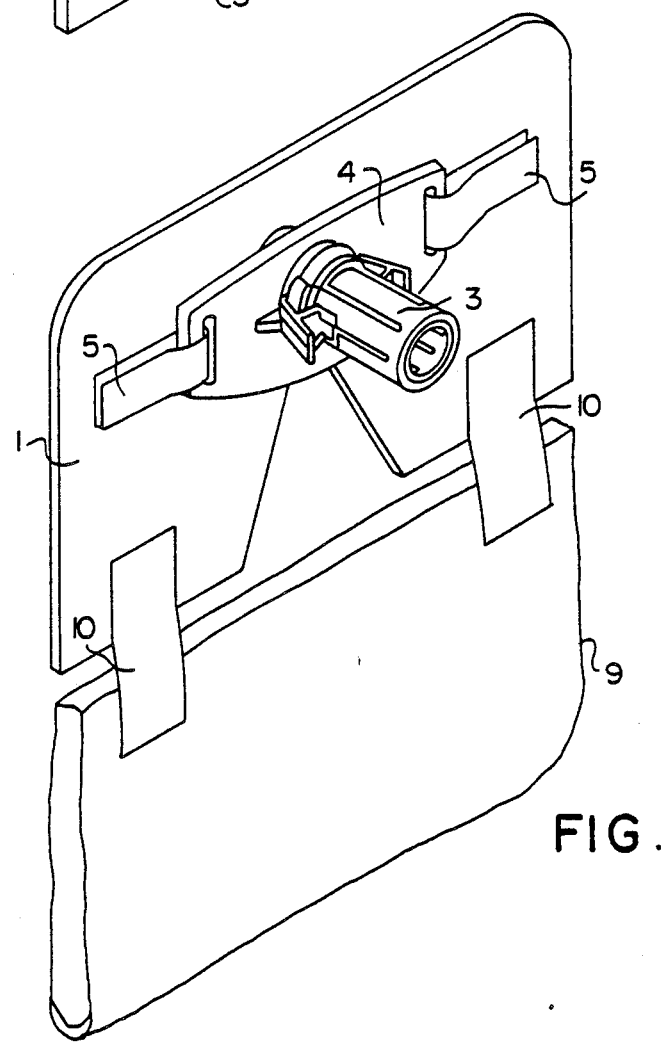
FIG. 4 is a frontal view comprising an occlusive dressing to which a tracheostomy tube and a secretion-absorbing pad is secured.

FIG. 4 shows a tie-less tracheostomy dressing complete with a secretion-absorbing/-collecting pad (9). The secretion-absorbing pad may be made of a cellulose material such as that used in the manufacture of disposible diapers. While the front-side of the pad is covered with a moisture-proof (e.g. plastic) barrier which serves to protect hospital gowns and clothing, the absorbent material on the back-side of the pad is exposed so as to collect secretions. The secretion-absorbing pad contains adhesive strips (10) which are used to attach the absorbent pad to the occlusive dressing.

Figure 5:
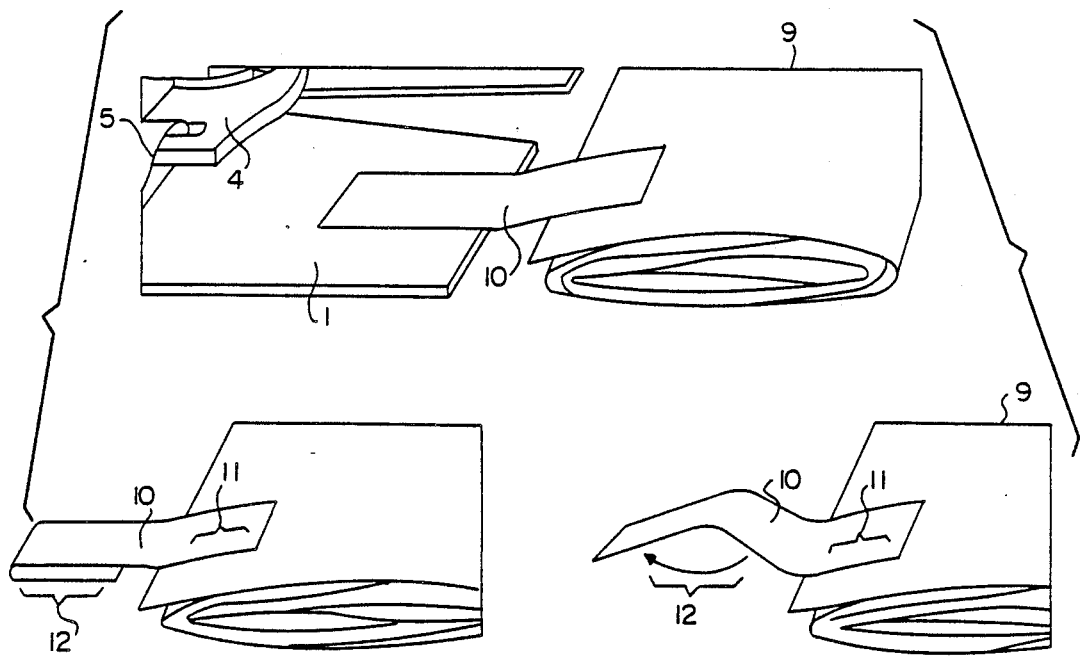
FIG. 5 illustrates how a secretion-absorbing pad is secured to the occlusive dressing.

FIG. 5 shows how the secretion absorbing pad is fastened to the occlusive dressing using the adhesive strips. Preferably, one end of the adhesive strips is permanently secured to the top of the pad (11) while the other side is a self-adhesive tab (12) that is folded back on itself. Self-adhesive tabs of the type conventionally used to secure disposable diapers may be adapted for use herein. When the self-adhesive tab is peeled back, the pad may be attached to the occlusive dressing. The secretion-absorbing pad not only collects secretions but acts to enhance healing by collecting secretions away from or distal to the tracheal site.

While the primary purpose of the secretion-absorbing pad is to promote healing via secretion collection, it also allows for more efficiency in terms of dressing change since it is the only part which needs to be frequently replaced and such replacement requires only one healthcare worker.

By the time the patient is ready to leave the hospital, the secretion collection pad should no longer be necessary. The patient goes home with a tracheostomy dressing substantially as shown in FIG. 3.

Alternative embodiments include impregnating the occlusive pectin based dressing with a broad spectrum antibiotic such as neosporine. This would further enhance the healing process by destroying surface bacteria. Such an impregnated dressing would most likely be used during the immediate post-operative period. This embodiment is particularly advantageous and efficient since a separate step would not be required for application of neosporine ointment to the wound. The elimination of the application step would also decrease incidence of healthcare worker cross-contamination.

Another embodiment is to include a moisture sensitive ingredient in the secretion-collection pad. A moisture indicator which produces a color change which would be observable through the moisture proof barrier when the pad reaches saturation is preferred. Various moisture indicators are known in the art and have been used in, for example, disposable diapers. Such a visual cue would serve to alert healthcare workers that the collection pad needs to be changed.

The collection pad could also be impregnated with an ingredient that would allow moisture to form a gel and "bead up". A preferred ingredient is sodium poliacrelate which is capable of absorbing 50 to 100 times its weight of liquid. The addition of such an ingredient would further discourage skin breakdown and enhance the healing process and the comfort of the patient.

The invention provides numerous advantages over the traditional method employing ties and a gauze dressing. The purpose of the gauze dressing of the prior art, which completely encircles the tracheal stoma, is to collect trachial secretions. Not only does the wet gauze act to irritate the skin but it serves as a potential medium for infection to occur. In contrast, the occlusive pectin based dressing which encircles approximately 60% of the tracheal opening does not act as an irritant to the newly excised skin. Not only is the occlusive dressing non-irritating, but it keeps the tracheal site free from tracheal secretions since the secretions are channeled away from the site to an absorbent pad located distal to the site. In terms of cosmetic appearance, the occlusive pectin based dressing is neutral in tone and may even be manufactured in a variety of skin tones so that the dressing is less visually obtrusive than a white gauze dressing. The disadvantage of conventional tracheostomy ties, which encircle the patient's neck and act to secure the tracheostomy tube are completely avoided since the invention does not use tracheostomy ties. As such, potential problems, e.g. irritation, skin breakdown, are also avoided.

In order to combat the disadvantages inherent in the prior art, tracheostomy dressings must be changed and the tracheal site cleansed every 8 hours, or more often if the gauze becomes saturated. Tracheostomy ties should be changed every 24 hours or more frequently if they become soiled. In contrast, the occlusive dressing of the invention is more efficient in that it needs changing every 48–72 hours. Further, while the changing of the ties and gauze of the prior art require the services of two healthcare workers every 8 or so hours, two healthcare workers are needed at intervals of 48 to 72 hours or longer in order to change the occlusive dressing of the invention. Between changes, the secretion collecting pad is easily replaced as needed and requires only one healthcare worker. In fact, when the pad becomes saturated, the pad may even be changed by the patient.

The invention is also advantageous in terms of cost. During a 12 day hospital stay, the post-operative tracheostomy care of a patient, in terms of nursing hours and material costs, when the traditional gauze-type dressing is employed, far exceeds the cost of the the same 12 day stay when the occlusive dressing of the type described herein is employed.

We claim:

1. A tracheostomy dressing comprising:
    an adhesive-backed impermeable membrane occlusive to air and water defining an outer periphery, said membrane having a centrally located key-hole shaped opening, which opening consists of a centrally located circular portion and, continuous therewith, a portion of the opening extending downwardly and widening outwardly from said circular portion of the opening to a portion of the periphery of said tracheostomy dressing, said key-hole shaped opening sized to allow for a tracheostomy tube to extend through the circular portion of the tracheostomy dressing, and
    a means for securing a tracheostomy tube to the dressing which consists of a two-sided strip having a first side and a second side and which has an adhesive means on part of the first side of said strip for securing part of the first side to said membrane and a self fastening means on the second side for securing said tracheostomy tube to said dressing.

2. The tracheostomy dressing of claim 1, wherein said self-fastening means are hooks and loops fasteners.

3. The tracheostomy dressing of claim 1 further comprising a moisture absorbing means which is attached to said membrane where said opening meets the periphery of said membrane.

4. The tracheostomy dressing of claim 3, wherein said membrane contains an antibiotic.

5. The tracheostomy dressing of claim 3, wherein said moisture absorbing means includes a moisture indicator.

6. A method of dressing a patient who has had a tracheostomy tube inserted through a tracheal incision comprising:
    pressing an impermeable adhesive-backed membrane, defining an outer periphery of a tracheostomy dressing, having a centrally located circular opening and, extending downwardly and widening outwardly from said circular opening and continuous therewith, an opening which extends to a portion of the periphery of said impermeable membrane, and which contains a skin-sensitive adhesive applicable to the neck of the patient such that the centrally located circular opening of said impermeable membrane is placed around the tracheal incision through which the tracheostomy tube passes, said tracheostomy tube having two flanges which extend out from opposite sides of the tracheostomy tube, each flange containing a slot,
    securing the tracheostomy tube to the impermeable membrane by passing a first strip having a first side and a second side, and which has an adhesive means on part of the first side of said first strip and a self-fastening means on the second side of said first strip, through the slot on one of said flanges, attaching the first strip to the impermeable membrane by said adhesive means and folding said second side of said strip back on itself so as to secure one side of the tracheostomy tube to the impermeable membrane and passing a second strip having a first side and a second side, and which has an adhesive means on part of the first side and a self-fastening means on the second side, through the slot on the other of said flanges, attaching the second strip to the impermeable membrane by said adhesive means and folding said second side of said second strip back on itself so as to secure the other side of the tracheostomy tube to the impermeable membrane, and
    attaching a moisture absorbing pad to the impermeable membrane at a portion of the periphery of said impermeable membrane.

7. The method of claim 6, wherein the moisture absorbing pad is replaced when it becomes saturated with tracheal secretions.

8. The method of claim 6, wherein said self-fastening means are hooks and loops fasteners.

9. The method of claim 6, wherein said membrane contains an antibiotic.

10. The method of claim 6, wherein said moisture absorbing means includes a moisture indicator.

* * * * *